United States Patent [19]

Henning et al.

[11] Patent Number: 4,691,022

[45] Date of Patent: Sep. 1, 1987

[54] PROCESS FOR THE PREPARATION OF MONOCYCLIC, BICYCLIC AND TRICYCLIC AMINOACIDS

[75] Inventors: Rainer Henning, Hattersheim am Main; Hansjörg Urbach, Kronberg/Taunus, both of Fed. Rep. of Germany

[73] Assignee: Hoechst Aktiengesellschaft, Fed. Rep. of Germany

[21] Appl. No.: 623,200

[22] Filed: Jun. 21, 1984

[30] Foreign Application Priority Data

Jun. 23, 1983 [DE] Fed. Rep. of Germany ....... 3322530

[51] Int. Cl.⁴ .......................................... C07C 103/52
[52] U.S. Cl. .................................. 548/408; 548/515; 548/452; 548/535; 548/526; 549/437
[58] Field of Search .............. 548/408, 515, 452, 535, 548/526; 549/434

[56] References Cited

PUBLICATIONS

*Hetrocyclic Chemistry An Introduction:* by Adrien Albert University of London, The Athlone Press 1959.
*Advanced Organic Chemistry:* Louis F. Fieser, Reinhold Publishing Corporation.

*Primary Examiner*—John Kight
*Assistant Examiner*—M. L. Moore

*Attorney, Agent, or Firm*—Finnegen, Henderson, Farabow, Garrett & Dunner

[57] ABSTRACT

The invention relates to a process for the preparation of compounds of the formula I

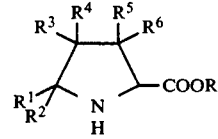

in which R represents hydrogen, alkyl or aralkyl, and $R^1$ to $R^6$ denote identical or different radicals hydrogen, alkyl, cycloalkyl, cycloalkylalkyl, cycloalkenylalkyl, aralkyl or aryl, both being monosubstituted, disubstituted or trisubstituted in the aryl moiety by alkyl, alkoxy, hydroxyl, halogen, nitro, methylenedioxy and/or cyano, or in which two of the radicals $R^1$ to $R^6$, together with the carbon atom(s) bearing them form a monocyclic or bicyclic ring system, and the remaining radicals are hydrogen, which process comprises converting, with an oxidizing agent in the presence of a silver salt, a pyrrolidine derivative of the formula II into a Δ¹-pyrroline derivative of the formula III, reacting the latter with hydrogen cyanide or a metal cyanide to form a nitrile of the formula IV, and subjecting the latter to solvolysis with a compound of the formula ROH.

7 Claims, No Drawings

PROCESS FOR THE PREPARATION OF MONOCYCLIC, BICYCLIC AND TRICYCLIC AMINOACIDS

The invention relates to a process for the preparation of compounds of the formula I

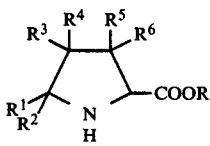

in which
R represents hydrogen, $(C_1-C_6)$-alkyl or $(C_7-C_9)$-aralkyl, and
$R^1$ to $R^6$ are identical or different and, independently of one another, denote hydrogen, $(C_1-C_8)$-alkyl, $(C_3-C_9)$-cycloalkyl, $(C_3-C_9)$-cycloalkyl-$(C_1-C_4)$-alkyl, $(C_5-C_9)$-cycloalkenyl-$(C_1-C_4)$-alkyl, $(C_6-C_{12})$-aryl-$(C_1-C_4)$-alkyl or $(C_6-C_{12})$-aryl, both of which can be monosubstituted, disubstituted or trisubstituted in the aryl moiety by $(C_1-C_4)$-alkyl, $(C_1-C_4)$-alkoxy, hydroxyl, halogen, nitro, methylenedioxy and/or cyano, or
in which
two of the radicals $R^1$ to $R^6$, together with the carbon atom bearing them or the two carbon atoms bearing them, form a 4- to 10-membered saturated or unsaturated monocyclic or bicyclic carbocyclic ring system, and the remaining radicals are hydrogen,
which process comprises converting a pyrrolidine derivative of the formula II

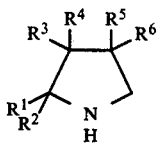

in which $R^1$ to $R^6$ have the same meaning as in formula I, with an oxidizing agent in the presence of a silver salt, into a $\Delta^1$-pyrroline derivative of the formula III

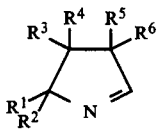

in which $R^1$ to $R^6$ have the same meaning as in formula I, reacting the latter with hydrogen cyanide or a cyanide to form a compound of the formula IV

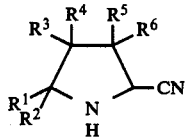

in which $R^1$ to $R^6$ have the same meaning as in formula I, and reacting the latter with a compound of the formula ROH, in which R has the meaning defined above, with the formation of a compound of the formula I.

The preparation of proline derivatives by the addition of hydrocyanic acid onto $\Delta^1$-pyrroline derivatives followed by hydrolysis is known in a few cases from the literature, but most of the necessary $\Delta^1$-pyrroline derivatives are prepared by very complicated routes (for example J. Chem. Soc. 1959, 2087). According to statements in the literature, the oxidation of cyclic amines to give the corresponding imines is usually an unfavorable reaction. The process suffers from the necessity to use toxic reagents (mercury salts) and from the fact that the yields are mostly very low (J. Chem. Soc. 1959, 2087). The exceptions to this are compounds having tertiary nitrogen atoms (for example J. Amer. Chem. Soc. 79, 5279 (1957)). However, the oxidation of these provides imine derivatives which, because of steric hindrance, do not add on hydrocyanic acid (J. Chem. Soc. 1959, 2087). In addition, oxidation of secondary amines is only successful with a few selected substituents on the five-membered ring. The oxidation of pyrrolidine by peroxodisulfate to give $\Delta^1$-pyrroline trimers is known from J. Chem. Soc., Perkin Trans. I 1982, 3031.

Starting from compounds of the formula IV, it is possible to prepare, by multistep synthetic routes, compounds of the formula I, few examples of each of these compounds being described in the literature. The types of synthetic routes which are suitable for this are electrochemical oxidation followed by reaction with phenyl isonitrile (Tetrahedron Lett. 1981, 2411) or trimethylsilyl cyanide (Tetrahedron Lett. 1981, 141), with Lewis acid catalysis in each case, followed by hydrolysis or chlorination in the α-position to the nitrogen, cyanide exchange and hydrolysis (European Pat. No. A 22,208).

The process according to the invention is particularly distinguished by the individual steps being straightforward to carry out, and the reagents used being of low cost and readily accessible. A preferred embodiment comprises preparing compounds of the formula I, in which
R has the abovementioned meaning,
$R^1$ to $R^6$ are identical or different and, independently of one another, denote hydrogen, methyl, ethyl, propyl, isopropyl, tert.-butyl, cyclopentyl, cyclohexyl, cycloheptyl, cyclopentylmethyl, cyclopentylethyl, cyclohexylmethyl, phenyl, naphthyl, 4-methoxyphenyl, 4-fluorophenyl, 4-chlorophenyl, 3,4-dimethoxyphenyl, 3,4-methylenedioxyphenyl, 3,4-dichlorophenyl, p-tolyl, benzyl, 4-methoxybenzyl, 4-chlorobenzyl, phenylethyl, 2-phenylpropyl or 1-phenylpropyl,
or in which two of the radicals $R^1$ to $R^6$ form, in the manner defined above, a cyclobutyl, cyclopentyl, cyclohexyl, cycloheptyl, cyclooctyl, bicyclo[2.2.1]heptyl or bicyclo[2.2.2]octyl ring, the bonds preferably starting from the same carbon atom or from neighbouring carbon atoms, and the remaining radicals being hydrogen.

A particularly preferred embodiment comprises preparing compounds of the formula 1, in which
R has the abovementioned meaning, but especially denotes hydrogen, tert.-butyl or benzyl, and
$R^1$ to $R^6$ denote hydrogen, or in which one or two of the radicals $R^1$ to $R^6$, independently of one another, denote methyl, ethyl, propyl, isopropyl, cyclopentyl, cyclohexyl, phenyl, 4-methoxyphenyl, 4-fluorophenyl, benzyl, phenethyl or 4-methoxybenzyl, and the others denote hydrogen, or two of the radicals $R^1$ to $R^6$, which are located on the same or on neighbouring carbon atoms, form together with the latter a cyclopentyl, cyclohexyl, cycloheptyl, bicyclo[2.2.1]heptyl or bicyclo[2.2.2]octyl ring, the remaining radicals denoting hydrogen.

Depending on the way it is carried out and the nature of the substituents $R^1$ to $R^6$, the process according to the invention provides the compounds of the formula I as mixtures of enantiomers or diastereomers or as pure diastereomers. Resulting mixtures can be separated into the constituents by suitable processes known per se, such as fractional crystallization or chromatography for diastereomers, or formation of diastereomeric salts, where appropriate of suitable derivatives, for mixtures of enantiomers. Where appropriate, this separation can also be carried out at the stage of the compounds of the formula IV. The following compounds of the formula I can be prepared in a very particularly advantageous manner using the process according to the invention.

Proline, cis-octahydroindole-2-exo-carboxylic acid, cis-octahydroindole-2-endo-carboxylic acid, trans-octahydroindole-2-α-carboxylic acid, trans-octahydroindole-2-β-carboxylic acid, cis-octahydrocyclopenta[b]pyrrole-2-exo-carboxylic acid, cis-octahydrocyclopenta[b]pyrrole-2-endo-carboxylic acid, trans-octahydrocyclopenta[b]pyrrole-2-α-carboxylic acid, trans-octahydrocyclopenta[b]pyrrole-2-β-carboxylic acid, 2-azaspiro[4,5]decane-3-carboxylic acid, 2-azaspiro[4,4]nonane-3-carboxylic acid, spiro[bicyclo[2.2.2]octane-2,3'-pyrrolidine]-5-exo-carboxylic acid, spiro[bicyclo[2.2.2]octane-2,3'-pyrrolidine]-5-endo-carboxylic acid, spiro[bicyclo[2.2.1]heptane-2,3'-pyrrolidine]-5-exo-carboxylic acid, cis-exo-3-azatricyclo[5.2.1.0$^{2,6}$]decane-4-exo-carboxylic acid, cis-exo-3-azatricyclo[5.2.1.0$^{2,6}$]decane-4-endocarboxylic acid, cis-endo-3-azatricyclo[5.2.1.0$^{2,6}$]decane-4-endo-carboxylic acid, cis-endo-3-azatricyclo[5.2.1.0$^{2,6}$]decane-4-exo-carboxylic acid, cis-decahydrocyclohepta[b]pyrrole-2-exo-carboxylic acid, cis-decahydrocyclohepta[b]pyrrole-2-endo-carboxylic acid, trans-decahydrocyclohepta[b]pyrrole-2-α-carboxylic acid, trans-decahydrocyclohepta[b]pyrrole-2-β-carboxylic acid, cis-octahydroisoindole-1-exo-carboxylic acid, cis-octahydroisoindole-1-endo-carboxylic acid, trans-octahydroisoindole-1-α-carboxylic acid, trans-octahydroisoindole-1-β-carboxylic acid, cis-octahydrocyclopenta[c]pyrrole-1-exo-carboxylic acid, 1-azaspiro[4.5]decane-2-carboxylic acid, 1-azaspiro[4.4]nonane-2-carboxylic acid, 4,5-cis-diethylproline, 4,5-cis-dimethylproline, 5,5-dimethylproline, 4,4-dimethylproline, 4,4-diethylproline, 3,3-dimethylproline, 4,5-cis-diphenylproline and 4-phenylproline and the esters of the abovementioned aminoacids.

The reaction of the pyrrolidine of the formula II to give the Δ$^1$-pyrroline of the formula III is carried out with suitable oxidizing agents, preferably with ammonium, alkali metal or alkaline earth metal peroxodisulfates, particularly sodium or potassium peroxodisulfate, with catalysis by silver salts, preferably silver nitrate, which are added in amounts of 0.1 to 5 mole-%. The reaction is carried out in protic polar solvents, preferably in aqueous solution at −20° to +80° C., preferably at 0° to +30° C.

The addition of hydrocyanic acid onto compounds of the formula III is carried out in such a manner that an alkali metal, alkaline earth metal or transition metal cyanide, preferably sodium or potassium cyanide, is added to a suspension or solution of the compound of the formula III in a protic polar solvent, preferably water, and an acid pH is set up by adding a mineral acid, such as hydrochloric acid, hydrobromic acid or sulfuric acid, or an organic acid, such as acetic acid or formic acid, at −10° to +120° C., preferably at 0° C. to 30° C.

Finally, the nitriles of the formula IV are hydrolyzed to give the compounds of the formula I according to the invention in a manner known per se under acidic or basic conditions, preferably with mineral acids, such as hydrochloric acid, hydrobromic acid or sulfuric acid, at 0° to 150° C., preferably at 60° to 120° C.

The esters can be prepared from the resulting aminoacids by the customary methods of peptide chemistry. It has also proved to be favorable to react the nitriles of the formula IV with appropriate alcohols, with acid catalysis (for example HCl), via the iminoesters to give the esters (compare, for example, Org. Synth., Coll. Vol. 2 310 [1943]).

Many of the pyrrolidine derivatives of the formula II used as starting materials are known from the literature or are prepared in a few steps by processes known in principle. Thus, for example, details on cis-octahydroindole are to be found in German Pat. No. A 2,302,198, on trans-octahydroindole in Yakugaku Zasshi 95, 889 (1975), on cis-octahydrocyclopenta[b]pyrrole in J. Org. Chem. 43, 54 (1978), on trans-octahydrocyclopenta[b]pyrrole in USSR Pat. No. 761,462, on 2-azaspiro[4.4]nonane and 2-azaspiro[4.5]decane in J. Med. Chem. 15, 129 (1972), on spiro[bicyclo[2.2.1]heptane-2,3'-pyrrolidine] in German Pat. No. A 2,321,057, on 1-azaspiro[4.4]nonane in U.S. Pat. No. 3,814,324, on octahydroisoindole in Collect. Czech. Chem. Commun. 40, 3904 (1975), on octahydrocyclopenta[c]pyrrole in German Pat. No. A 2,415,064, on 2,3-dimethylpyrrolidine in J. Organomet. Chem. 181, 255 (1979), on 3-phenylpyrrolidine in Japan Kokai 74-72,266 and on a number of other derivatives in Arzneim.-Forsch. 12, 2089 (1971).

The compounds of the formula I are valuable intermediates in the preparation of pharmaceuticals, especially of inhibitors of angiotensin converting enzyme (ACE). Compounds of this type are known from, for example, European Pat. No. A 50,800 or are dealt with in German Patent Application No. P 31 51 690.4. Examples of this type of ACE inhibitor are substituted acyl derivatives of the formula V,

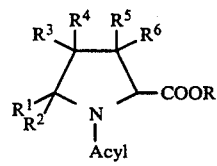

in which R and $R_1$ to $R_4$ are defined as above, $R^5$ and $R^6$ denote hydrogen, and acyl represents, for example, a radical of the formula VI

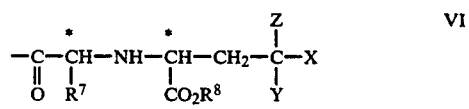

in which
$R^7$ denotes hydrogen, $(C_1-C_6)$-alkyl which can optionally be substituted by amino, $(C_1-C_4)$-acylamino or benzoylamino, $(C_2-C_6)$-alkenyl, $(C_5-C_9)$-cycloalkyl, $(C_5-C_9)$-cycloalkenyl, $(C_5-C_7)$- cycloalkyl-($C_1$-$C_4$)-alkyl, aryl or partially hydrogenated aryl, each of which can be substituted by ($C_1$-$C_2$)-alkyl, ($C_1$-$C_2$)-alkoxy or halogen, aryl-($C_1$-$C_4$)-alkyl, the aryl radical of which can be substituted as defined above, a monocyclic or bicyclic heterocyclic radical having 5 to 7 or 8 to 10 ring atoms respectively, 1 or 2 of these ring atoms being sulfur or oxygen atoms and/or 1 to 4 of these ring atoms being nitrogen atoms, or a side chain of an aminoacid, $R^8$ denotes hydrogen, ($C_1$-$C_6$)-alkyl, ($C_2$-$C_6$)-alkenyl or aryl-($C_1$-$C_4$)-alkyl, Y denotes hydrogen, Z denotes hydrogen, or Y and Z together denote oxygen, X denotes ($C_1$-$C_6$)-alkyl, ($C_2$-$C_6$)-alkenyl, ($C_5$-$C_9$)-cycloalkyl, aryl, which can be monosubstituted, disubstituted or trisubstituted by ($C_1$-$C_4$)-alkyl, ($C_1$-$C_4$)-alkoxy, hydroxyl, halogen, nitro, amino, ($C_1$-$C_4$)-alkylamino, di-($C_1$-$C_4$)-alkylamino and/or methylenedioxy, or 3-indolyl, and their physiologically acceptable salts.

Compounds of the formula V can be prepared by, for example, N-acylation of suitable esters of compounds of the formula I, such as, for example, benzyl or tert.butyl esters, using compounds of the formula Acyl—OH, in which Acyl is defined as above, followed by splitting off the ester groups by hydrogenolysis or with acid or base.

The condensation of esters of compounds of the formula I with compounds of the formula Acyl-OH is preferably carried out by known methods of peptide chemistry. Processes which provide adequate protection from racemization are particularly preferred, such as, for example, the DCC/HOBt method or the alkanephosphonic anhydride method described in U.S. Pat. No. 4,331,592.

The compounds of the formula V have a long-lasting and powerful hypotensive effect. On oral administration, they are well absorbed and they can be used for controlling hypertension of various etiologies and can be used alone or combined with other compounds having hypotensive, vasodilator or diuretic activity. Administration can be intravenously, subcutaneously or orally, oral administration being preferred. As a rule, the dose for oral administration is 0.01 to 10 mg/kg per day.

This can also be increased in severe cases, since toxic properties have not hitherto been observed. It is also possible to reduce the dose and this is particularly appropriate when diuretics are administered concurrently. The single dose for intravenous and subcutaneous administration should be between 0.1 and 250 µg per day.

The Examples which follow are intended to illustrate the invention without restricting it to the examples described.

EXAMPLE 1

Proline (a) $\Delta^1$-Pyrroline trimer

A solution of 4.05 g (0.015 mole) of potassium peroxodisulfate in 20 ml of water is added dropwise, at 0° C., to a stirred mixture of 1.06 g (0.015 mole) pyrrolidine, 1.2 g (0.03 mole) of sodium hydroxide and 12.7 mg (0.075 mmol) of silver nitrate in 15 ml of water, and the mixture is stirred for 2.5 hours. After saturating with sodium chloride, the solution is extracted with dichloromethane, the extracts are dried over sodium sulfate and concentrated at 0° C. in a rotary evaporator. 0.53 g of title compound is obtained as an oil.

$^1$H-NMR data (CDCl$_3$): $\delta$=1.2–2.1 (m, 12H), 2.1–2.5 (m, 3H), 3.0–3.2 (m, 6H) ppm.

(b) 2-Cyanopyrrolidine 0.53 g of $\Delta^1$-pyrroline trimer (0.0075 mole) are suspended in 5 ml of H$_2$O, 0.5 g of potassium cyanide are added and then, at 0° C., 5 ml of 2N hydrochloric acid are added dropwise. After 15 hours at room temperature, the mixture is extracted with ethyl acetate, and the aqueous phase is made alkaline with 2N NaOH and extracted with CH$_2$Cl$_2$. The dichloromethane extract is dried over sodium sulfate and concentrated. 0.4 g of oil is obtained.

$^1$H-NMR data (CDCl$_3$): $\delta$=3.8–3.6 (m, 1H), 3.4–3.0 (m, 2H), 1.8–1.2 (m, 4H) ppm.

(c) Proline 0.4 g of 2-cyanopyrrolidine are dissolved in 5 ml of 5N hydrochloric acid and boiled under reflux for 2 hours. After cooling, the mixture is concentrated, the residue is taken up in H$_2$O, the pH is adjusted to 5 using Amberlite ® IRA 93 (OH form), and the mixture is filtered and concentrated. Trituration with isopropyl ether provides 0.3 g of proline. Melting point 210° C. (decomposition).

EXAMPLE 2 cis-Octahydroindole-2-carboxylic acid (a) cis-3,3a,4,5,6,7,7a-Hexahydroindole 6 g (0.048 mole) of cis-octahydroindole are reacted with 13.5 g (0.05 mole) of potassium peroxodisulfate, 4 g of sodium hydroxide and 0.1 g of silver nitrate in 200 ml of water by the process described in Example 1a. 4 g of the title compound are obtained as an oil.

$^1$H-NMR data (CDCl$_3$): $\delta$=7.3 (br. s. 1H), 4.6–4.3 (m, 1H), 4.0–1.3 (m, 11H) ppm.

(b) 2-Cyano-cis-octahydroindole 4 g of cis-3,3a-4,5,6,7,7a-hexahydroindole are reacted with 2.1 g of potassium cyanide and 21 ml of 2N hydrochloric acid by the process described in Example 1b. 3.9 g of the title compound are obtained as an oil.

$^1$H-NMR data (CDCl$_3$): $\delta$=4.2–3.5 (m, 2H), 3.0–1.1 (m, 11H) ppm.

(c) cis-Octahydroindole-2-carboxylic acid 3.9 g of 2-cyano-cis-octahydroindole are reacted with 5N hydrochloric acid (50 ml) by the process described in Example 1c. A 2:1 mixture of cis-octahydroindole-2-oxo-carboxylic acid (2A) and cis-octahydroindole-2-endo-carboxylic acid (2B) is obtained, it being possible to separate these by chromatography on silica gel and crystallization from ethanol/acetone. Rf values (SiO$_2$, mobile phase CH$_2$Cl$_2$/MeOH/HOAc/H$_2$O=10:5:1:1)

2A: 0.67
2B: 0.62
Melting points:
2A: amorphous powder.
2B: 230°–233° C.

EXAMPLE 3 trans-Octahydroindole-2-carboxylic acid 2 g of a 1:1 mixture of trans-octahydroindole-2-$\alpha$-carboxylic acid (3A) and trans-octahydroindole-2-$\beta$-carboxylic acid (3B), melting point 280° C., is obtained from trans-octahydroindole (4.5 g) by the process steps described in Example 1a–c. The isomers can be separated by crystallization from ethanol/acetone.

EXAMPLE 4 cis-Octahydrocyclopenta[b]pyrrole-2-carboxylic acid

A 2.7:1 mixture of cis-octahydrocyclopenta[b]pyrrole-2-exo-carboxylic acid (4A) and cis-octahydrocyclopenta[b]pyrrole-2-endo-carboxylic acid (4B) is obtained from cis-octahydrocyclopenta[b]pyrrole by the process steps described in Example 1a–c. After taking up in acetone, pure 4A crystallizes out, melting point >180° C. (decomposition).

Pure 4B of melting point 205°–209° C., hydrochloride, can be obtained from the mother liquor of the crystallization.

EXAMPLE 5 trans-Octahydrocyclopenta[b]pyrrole-2-carboxylic acid trans-Octahydrocyclopenta[b]pyrrole is reacted by the process described in Example 1a–c to give a 1:1 mixture of trans-octahydrocyclopenta[b]pyrrole-2-α-carboxylic acid (5A) and trans-octahydrocyclopenta[b]pyrrole-2-β-carboxylic acid (5B). Pure 5B can be obtained by crystallization from acetone/ethanol, melting point >250° C. (decomposition).
Yield 35%

EXAMPLE 6

2-Azaspiro[4.5]decane-3-carboxylic acid

The title compound is obtained mixed with minor amounts of 2-azaspiro[4.5]decane-1-carboxylic acid, from which it can be separated pure by crystallization from ethanol/acetone, from 2-azaspiro[4.5]decane by the process described in Example 1a–c.
Yield 30%
Melting point 205° C. (decomposition)

EXAMPLE 7

2-Azaspiro[4.4]nonane-3-carboxylic acid

The title compound is obtained mixed with small amounts of 2-azaspiro[4.4]nonane-1-carboxylic acid, from which it can be obtained pure by crystallization from ethanol/acetone, from 2-azaspiro[4.4]nonane by the process described in Example 1a–c.
Yield 27%
amorphous powder
$^1$H-NMR data (D$_2$O): 4.02 (t, 1H), 2.3 (s, 2H), 2.0–1.1 (m, 1 OH) ppm.

EXAMPLE 8

5'-Cyanospiro[bicyclo[2.2.2]octane-2,3'-pyrrolidine]

(a) Spiro[bicyclo[2.2.2]octane-2,3'-pyrroline-Δ3']

3.0 g of the title compound are obtained as an oil, mixed with its trimers, from 4.3 g of spiro[bicyclo[2.2.2]octane-2,3+-pyrrolidine] by the process described in Example 1a.

(b) 5'-Cyanospiro[bicyclo[2.2.2]octane-2,3'-pyrrolidine]

3 g of the compound from 8a are dissolved in 100 ml of water with 2.25 g of potassium cyanide. While cooling in ice, 24 ml of 2N hydrochloric acid are added dropwise, and the mixture is stirred at room temperature for 72 hours. After extraction with ethyl acetate, the aqueous solution is made alkaline with 1N NaOH, extracted with ether and the extracts are dried over sodium sulfate. After concentrating, the crude product is chromatographed on silica gel using ethyl acetate/cyclohexane (1:1) as the mobile phase, by which means the endo and exo isomers are separated.

endo isomer (8bA): 0.83 g, melting point 78°–80° C.
$^1$H-NMR data (CDCl$_3$): δ=4.0 (t, J=14 Hz, 1H), 2.8 (s, 2H), 2.4 (s, 1H), 2.0 (d, 2H), 1.5 (br. s, 12H) ppm.
exo isomer (8bB): 1.5 g, melting point 38°–40° C.
$^1$H-NMR data (CDCl$_3$): δ=4.02 (X part of a ABX system, 1H), 2.85 (AB system, J=15 Hz, 2H), 2.5–1.0 (m, 15H) ppm.

EXAMPLE 9

Spiro[bicyclo[2.2.2]octane-2,3'-pyrrolidine]-5'-endo-carboxylic acid 0.9 g of the title compound, melting point 236° C., is obtained from 0.8 g of compound 8bA by the process described in Example 1c.
$^1$H-NMR data (D$_2$O): δ4.2 (X part of a ABX system, 1H) 3.2 (s, 2H), 2.5–1.5 (AB part of a ABX system, 2H), 1.5 (br. s, 12H) ppm.
Mass spectrum (m/e): 209 (M$^+$, 0.8%), 165 (13%), 164 (M—COOH, 100%), 87 (14%), 69 (10%).

EXAMPLE 10

Spiro[bicyclo[2.2.2]octane-2,3'-pyrrolidine]-5'-exo-carboxylic acid 1.4 g of the title compound are obtained from 1.5 g of compound 8bB by the process described in Example 1c, melting point 242° C.
$^1$H-NMR data (D$_2$O): δ=4.15 (X part of a ABX system, 1H), 3.2 (AB system, J=15 Hz, 1H), 2.5–1.7 (AB part of an ABX system, 2H), 1.5 (br. s, 12H) ppm.

EXAMPLE 11

Spiro[bicyclo[2.2.1]heptane-2,3'-pyrrolidine]-5'-exo-carboxylic acid

The title compound is obtained as a colorless amorphous powder, a mixture of isomers, from spiro[bicyclo[2.2.1]heptane-2,3'-pyrrolidine] by the process described in Example 1a–c.
Yield 24%
$^1$H-NMR data (D$_2$O): δ=4.3–4.0 (m, 1H), 3.5 (m, AB system, 2H), 2.5–1.0 (m, 12H) ppm.

EXAMPLE 12 cis-exo-3-Azatricyclo[5.2.1.0$^{2,6}$]decane-4-carboxylic acid

A 1:1 mixture of 4-exo-cyano-cis-exo-3-azatricyclo[5.2.1.0$^{2,6}$]decane and 4-endo-cyano-cis-exo-3-azatricyclo[5.2.1.0$^{2,6}$]decane is obtained from cis-exo-3-azatricyclo[5.2.1.0$^{2,6}$]decane by the process described in Examples 1a and b, the isomers are separated by chromatography on silica gel and hydrolyzed to give the exo and endo isomers of the title compound by the process described in Example 1c.

exo isomer: R$_f$ 0.54 (silica gel; CH$_2$Cl$_2$/MeOH/HOAc, H$_2$O=20:15:2:4).
endo isomer: R$_f$ 0.51 (silica gel; CH$_2$Cl$_2$/MeOH/HOAc, H$_2$O=20:15:2:4).

EXAMPLE 13 cis-endo-3-Azatricyclo[5.2.1.0²,⁶]decane-4-carboxylic acid

The exo and endo isomers of the title compound in the ratio 8:1 are obtained from cis-endo-3-azatricyclo[5.2.1.0²,⁶]decane as described in Example 12 using the process described in Example 1a–c.

exo isomer: R$_f$ 0.61 (silica gel; CH$_2$Cl$_2$/MeOH/HOAc, H$_2$O=20:15:2:4).

endo isomer: R$_f$ 0.66 (silica gel; CH$_2$Cl$_2$/MeOH/HOAc, H$_2$O=20:15:2:4).

EXAMPLE 14 cis-Decahydrocyclohepta[b]pyrrole-2-carboxylic acid

A 2:1 mixture of the exo and endo isomers of the title compound, which can be separated by crystallization from ethanol/acetone or by chromatography of the nitrile precursors on silica gel, is obtained from 5.2 g of cis-decahydro-2-azaazulene by the process described in Examples 1a to c.

exo isomer (14A) amorphous powder endo isomer (14B) colorless crystals, melting point 252°–256° C.

EXAMPLE 15 trans-Decahydrocyclohepta[b]pyrrole-2-carboxylic acid

The title compound is obtained as a 1:1 mixture of the α and β isomers, which cannot be separated, from trans-decahydro-2-azaazulene by the process described in Example 1a to c.

EXAMPLE 16 cis-Octahydroisoindole-1-carboxylic acid

A mixture of 5 parts of 1-exo-cyano-cis-octahydroisoindole (NMR (CDCl$_3$): δ=3.8 (d, 1H)) and 1 part of 1-endo-cyano-cis-octahydroisoindole (NMR (CDCl$_3$): δ=4.0 (d, 1H)) is obtained from 0.8 g of cis-octahydroisoindole by the process described in Example 1a and b.

After separating the isomers on silica gel using ethyl acetate/cyclohexane (1:1) as the mobile phase, they are hydrolyzed by the process described in Example 1c. 0.3 g of cis-octahydroisoindole-1-exo-carboxylic acid (16A) and 0.05 g of cis-octahydroisoindole-1-endo-carboxylic acid (16B) are obtained, each as colorless powders.

EXAMPLE 17 trans-Octahydroisoindole-1-carboxylic acid

Starting from trans-octahydroisoindole, a 1:1 mixture of trans-octahydroisoindole-1-α-carboxylic acid (17A) and trans-octahydroisoindole-1-β-carboxylic acid (17B) is obtained in 27% yield by the process described in Example 1a–c.

R$_f$=0.65 (SiO$_2$; CH$_2$Cl$_2$/MeOH/HOAc/H$_2$O=10:5:1:1)

EXAMPLE 18 cis-Octahydrocyclopenta[c]pyrrole-1-exo-carboxylic acid

Starting from cis-octahydrocyclopenta[c]pyrrole, the title compound is obtained in 34% yield by the process described in Example 1a–c.

Melting point 190°–195° C. after crystallization from ethanol/diisopropyl ether.

EXAMPLE 19

1-Azaspiro[4.5]decane-2-carboxylic acid

The title compound is obtained in 30% yield from 1-azaspiro[4.5]decane by the process described in Example 1a–c. Colorless crystals of melting point 129°–132° C. (frome acetone/diisopropyl ether).

EXAMPLE 20

1-Azaspiro[4.4]nonane-2-carboxylic acid

The title compound is obtained as a colorless amorphous powder in 18% yield from 1-azaspiro[4.4]nonane by the process described in Example 1a–c.

EXAMPLE 21

4,5-cis-Diethylproline

The isomers with the carboxyl groups in the cis position to the ethyl groups (21A), melting point 230°–35° C. (decomposition) and in the trans position to the ethyl groups (21B, melting point 158°–162° C.) are obtained, after chromatographic separation of the nitrile stages and separate hydrolysis with hydrochloric acid, from 4,5-cis-diethylpyrrolidine by the process described in Example 1a–c.

We claim:

1. A process for the preparation of a compound of the formula

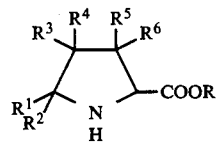

in which

R represents hydrogen, (C$_1$–C$_6$)-alkyl or (C$_7$–C$_9$)-aralkyl, and R$^1$ and R$^3$, together with the two carbon atoms bearing them, form a 4- to 8-membered saturated monocyclic or bicyclic carbocyclic ring system selected from cyclobutane, cyclopentane, cyclohexane, cycloheptane, cyclooctane, bicyclo[2.2.1]heptane or bicyclo[2.2.1]octane and the remaining radicals R$^2$, R$^4$, R$^5$ and R$^6$ are hydrogen, which process comprises converting a pyrrolidine derivative of the formula II

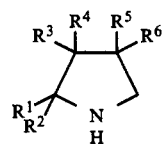

in which R$^1$ to R$^6$ have the same meaning as in formula I, with an ammonium, alkali metal or alkaline earth metal peroxodisulfate in the presence of a silver salt, into a Δ$^1$-pyrroline derivative of the formula III

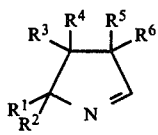

III in which $R^1$ to $R^6$ have the same meaning as in formula I, reacting the latter with hydrogen cyanide or a metal cyanide to form a compound of the formula IV

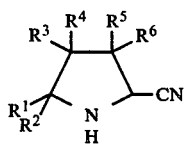

IV in which $R^1$ to $R^6$ have the same meaning as in formula I, and reacting the latter with a compound of the formula ROH, in which R has the meaning defined above, with the formation of a compound of the formula I.

2. The process as claimed in claim 1, wherein is prepared a compound of the formula I

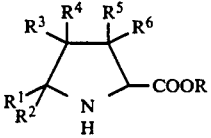

I in which R has the meaning defined in claim 7, and $R^1$ and $R^3$ form, together with the two carbon atoms bearing them, a cyclopentane, cyclohexane, cycloheptane, bicyclo[2.2.1]heptane or bicyclo[2.2.2]octane ring, the remaining radicals $R^2$, $R^4$, $R^5$, and $R^6$ denoting hydrogen.

3. The process as claimed in claim 1, wherein is prepared cis-octahydro-cyclopenta[b]pyrrole-2-carboxylic acid.

4. The process as claimed in claim 1, wherein is prepared cis-octahydroindole-2-carboxylic acid.

5. The process as claimed in claim 1, wherein is prepared trans-octahydroindole-2-carboxylic acid.

6. The process as claimed in claim 1, wherein a compound of the formula IV is reacted with water.

7. The process as claimed in claim 1, wherein a compound of the formula IV is reacted with a compound of the formula ROH, in which R has the meanings defined in claim 1 with the exception of that of hydrogen, in the presence of an acid.

* * * * *